United States Patent
Marnfeldt

(10) Patent No.: US 11,331,495 B2
(45) Date of Patent: May 17, 2022

(54) STIMULATION FIELD MODELLING IN AN IMPLANTABLE STIMULATOR DEVICE

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 83 days.

(21) Appl. No.: 16/442,073

(22) Filed: Jun. 14, 2019

(65) Prior Publication Data

US 2020/0001091 A1    Jan. 2, 2020

Related U.S. Application Data

(60) Provisional application No. 62/690,422, filed on Jun. 27, 2018.

(51) Int. Cl.
*A61N 1/36* (2006.01)
*A61N 1/372* (2006.01)

(52) U.S. Cl.
CPC ..... *A61N 1/36185* (2013.01); *A61N 1/36157* (2013.01); *A61N 1/37241* (2013.01); *A61N 1/37247* (2013.01); *A61N 1/37288* (2013.01)

(58) Field of Classification Search
CPC ............ A61N 1/36185; A61N 1/36157; A61N 1/327241; A61N 1/37247; A61N 1/37288
See application file for complete search history.

(56) References Cited

U.S. PATENT DOCUMENTS

| 4,964,407 A | 10/1990 | Baker, Jr. et al. |
| 6,181,969 B1 | 1/2001 | Gord |

(Continued)

FOREIGN PATENT DOCUMENTS

| WO | WO-2007097861 A1 * | 8/2007 | ......... A61N 1/36157 |
| WO | WO-2007100428 A1 * | 9/2007 | ........... A61N 1/0529 |
| WO | WO-2014071445 A1 * | 5/2014 | ........... A61B 5/4848 |

OTHER PUBLICATIONS

Bera T. K. (2014). Bioelectrical Impedance Methods for Noninvasive Health Monitoring: A Review. Journal of medical engineering, 2014, 381251. https://doi.org/10.1155/2014/381251 (Year: 2014).*

(Continued)

*Primary Examiner* — Shirley X Jian
(74) *Attorney, Agent, or Firm* — Lewis & Reese, PLLC

(57) ABSTRACT

A field measurement algorithm and measuring circuitry in an implantable stimulator, and an field modelling algorithm operable in an external device, are used to determine an electric field in a patient's tissue. The field measuring algorithm provides at least one test current between two electrodes, and a plurality of voltage differentials are measured at different combinations of the electrodes. The voltage differential data is telemetered to the field modelling algorithm which determines directional resistance at different locations in the patient's tissue. The field modelling algorithm can then use a stimulation program selected for the patient and the determined directional resistances to determine voltages in the patient's tissue at various locations, which in turn can be used to model a more-accurate electric field in the tissue, and preferably to render an electric field image for display in a graphical user interface of the external device.

19 Claims, 11 Drawing Sheets

(56) References Cited

U.S. PATENT DOCUMENTS

| | | | |
|---|---|---|---|
| 6,516,227 B1 | 2/2003 | Meadows et al. | |
| 8,463,402 B2 | 6/2013 | Zhu et al. | |
| 8,548,596 B2* | 10/2013 | Gerber | A61M 5/14276 |
| | | | 607/59 |
| 8,606,362 B2 | 12/2013 | He et al. | |
| 8,620,436 B2 | 12/2013 | Parramon et al. | |
| 8,655,453 B2* | 2/2014 | Werder | A61N 1/36185 |
| | | | 607/74 |
| 8,731,679 B2 | 5/2014 | Ternes et al. | |
| 8,761,897 B2 | 6/2014 | Kaula et al. | |
| 8,768,453 B2 | 7/2014 | Parramon et al. | |
| 8,805,525 B2* | 8/2014 | Gerber | A61N 1/36071 |
| | | | 607/59 |
| 8,958,870 B2* | 2/2015 | Gerber | A61N 1/37247 |
| | | | 607/2 |
| 9,061,140 B2 | 6/2015 | Shi et al. | |
| 9,089,704 B2 | 7/2015 | Kelly | |
| 9,259,574 B2 | 2/2016 | Aghassian et al. | |
| 9,446,243 B2 | 9/2016 | Marnfeldt et al. | |
| 9,724,508 B2 | 8/2017 | Lamont et al. | |
| 9,814,885 B2* | 11/2017 | Molnar | A61N 1/0529 |
| 10,285,646 B1 | 5/2019 | Grant | A61N 1/36128 |
| 10,980,480 B2* | 4/2021 | Grant | A61N 1/36128 |
| 2003/0139781 A1* | 7/2003 | Bradley | A61N 1/0551 |
| | | | 607/48 |
| 2008/0058656 A1* | 3/2008 | Costello | A61B 5/1107 |
| | | | 600/508 |
| 2008/0319497 A1 | 12/2008 | Griffith et al. | |
| 2009/0157155 A1* | 6/2009 | Bradley | A61N 1/37247 |
| | | | 607/116 |
| 2010/0185268 A1* | 7/2010 | Fowler | A61N 1/0529 |
| | | | 607/116 |
| 2011/0040353 A1* | 2/2011 | Gerber | A61N 1/36146 |
| | | | 607/59 |
| 2011/0040546 A1* | 2/2011 | Gerber | A61N 1/37 |
| | | | 703/11 |
| 2011/0106215 A1* | 5/2011 | Moffitt | A61N 1/37247 |
| | | | 607/60 |
| 2011/0112609 A1 | 5/2011 | Peterson | |
| 2011/0270348 A1* | 11/2011 | Goetz | A61N 1/372 |
| | | | 607/45 |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2012/0191153 A1 | 7/2012 | Swerdlow et al. | |
| 2013/0085361 A1* | 4/2013 | Mercanzini | A61B 5/24 |
| | | | 600/377 |
| 2013/0085362 A1* | 4/2013 | Choi | A61B 5/0536 |
| | | | 600/378 |
| 2013/0184794 A1 | 7/2013 | Feldman et al. | |
| 2014/0031901 A1* | 1/2014 | Zhu | A61N 1/36125 |
| | | | 607/60 |
| 2015/0080982 A1 | 3/2015 | Funderburk | |
| 2015/0157861 A1 | 6/2015 | Aghassian | |
| 2015/0216435 A1* | 8/2015 | Bokan | A61N 1/3629 |
| | | | 600/515 |
| 2015/0231402 A1 | 8/2015 | Aghassian | |
| 2015/0360038 A1 | 12/2015 | Zottola et al. | |
| 2016/0184591 A1 | 6/2016 | Feldman et al. | |
| 2017/0281958 A1 | 10/2017 | Serrano Carmona et al. | |
| 2018/0064930 A1 | 3/2018 | Zhang et al. | |
| 2018/0071513 A1 | 3/2018 | Weiss et al. | |
| 2018/0071520 A1 | 3/2018 | Weerakoon et al. | |
| 2018/0071527 A1 | 3/2018 | Feldman et al. | |
| 2018/0140831 A1 | 5/2018 | Feldman et al. | |
| 2018/0264278 A1 | 9/2018 | Laghi | |
| 2018/0339156 A1* | 11/2018 | Nash | A61N 1/0551 |
| 2019/0076659 A1 | 3/2019 | Steinke et al. | |
| 2019/0083796 A1 | 3/2019 | Weerakoon et al. | |
| 2019/0099606 A1 | 4/2019 | Shah et al. | |
| 2019/0134383 A1 | 5/2019 | Brill et al. | |
| 2019/0343462 A1* | 11/2019 | Grant | A61B 5/7221 |

OTHER PUBLICATIONS

International Search Report and Written Opinion regarding corresponding PCT Application No. PCT/US2019/037314, dated Oct. 9, 2019.

H.M. Loke, "Tutorial: 2-D and 3-D Electrical Imaging Surveys," (2004), published at https://sites.ualberta.ca/ ~unsworth/ UA-classes/ 223/ loke_course_notes.pdf.

W. Daily et al., "Electrical Resistance Tomography—Theory and Practice," Near-Surface Geophysics Part 2: Applications and Case Histories, Chap. 17, pp. 573-598 (2005).

"Electrical Impedance Tomography," published at https:// en.wikipedia.org/ wiki/Electrical_impedance_tomography.

"Electrical Capacitance Volume Tomography," published at https://en.wikipedia.org/ wiki/Electrical_capacitance_volume_tomography.

Vercise PC Deep Brain Stimulation System: Vercise Navigator 1.0 Programming Guide, Boston Scientific, NM-320907-AA, Jan. 2016, 16 pages.

Guide™ DBS Software Programming Manual: Directions for Use, Boston Scientific, 91062299-02 Rev A, published at http://www.bostonscientific.com/content/dam/Manuals/eu/current-rev-en/91062299-02_Rev_A_GUIDE_DBS_Software_Programming_Manual_DFU_multi_OUS_s.pdf (date unknown).

* cited by examiner

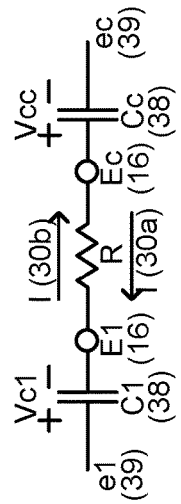
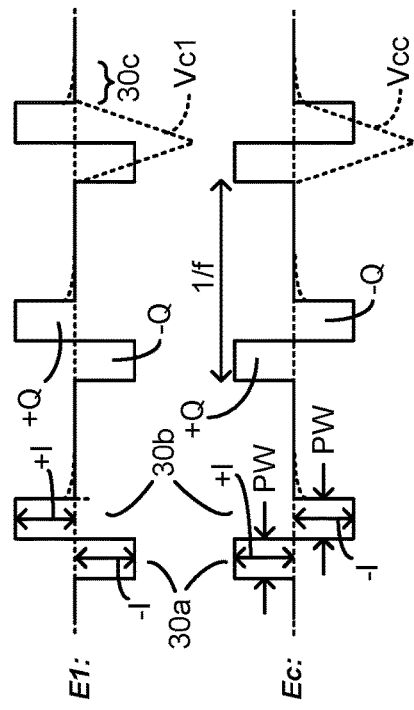
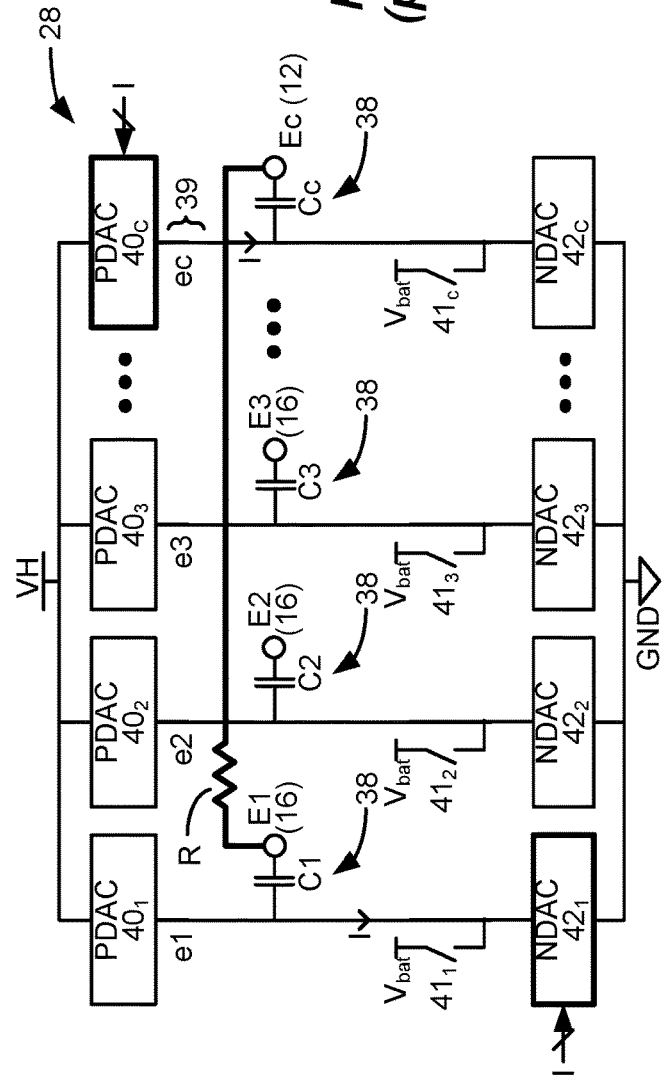

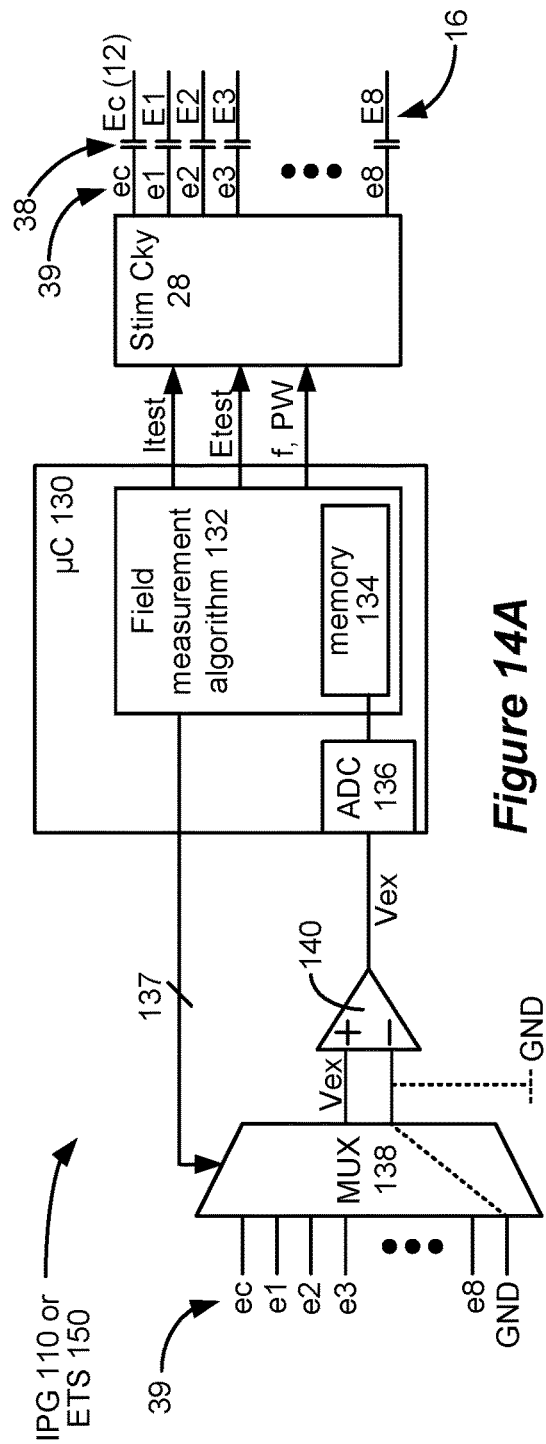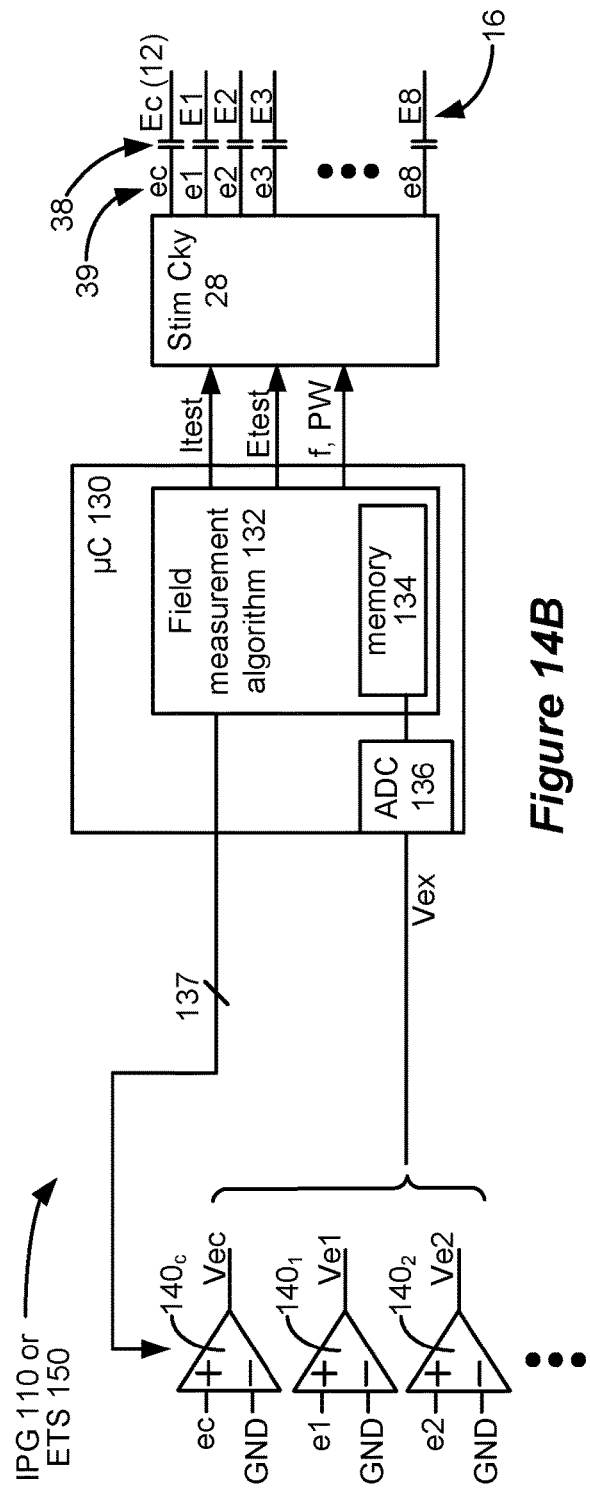

STIMULATION FIELD MODELLING IN AN IMPLANTABLE STIMULATOR DEVICE

CROSS REFERENCE TO RELATED APPLICATIONS

This is a non-provisional application of U.S. Provisional Patent Application Ser. No. 62/690,422, filed Jun. 27, 2018, to which priority is claimed, and which is incorporated by reference in its entirety.

FIELD OF THE INVENTION

This application relates to Implantable Stimulator Devices (ISD), and more specifically to circuitry and methods for modelling a stimulation field in an ISD.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) or Spinal Cord Stimulation (SCS) system, such as that disclosed in U.S. Pat. No. 6,516,227 and U.S. Patent Application Publication 2016/0184591. However, the present invention may find applicability with any implantable neurostimulator device system.

A DBS or SCS system typically includes an Implantable Pulse Generator (IPG) 10 shown in FIG. 1A. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped electrodes 16 carried on a flexible body 18. In another example, a paddle lead 19 provides electrodes 16 positioned on one of its generally flat surfaces.

In yet another example shown in FIG. 1B, a percutaneous lead 33 can include one or more split-ring electrodes. In this example, eight electrodes 16 (E1-E8) are shown. Electrode E8 at the distal end of the lead and electrode E1 at a proximal end of the lead comprise ring electrodes spanning 360 degrees around a central axis of the lead 33. Electrodes E2, E3, and E4 comprise split-ring electrodes, each of which are located at the same longitudinal position along the central axis 31, but with each spanning less than 360 degrees around the axis. For example, each of electrodes E2, E3, and E4 may span 90 degrees around the axis 31, with each being separated from the others by gaps of 30 degrees. Electrodes E5, E6, and E7 also comprise split-ring electrodes, but are located at a different longitudinal position along the central axis 31 than are split ring electrodes E1, E2, and E3. As shown, the split-ring electrodes E1-E3 and E5-E7 may be located at longitudinal positions along the axis 31 between ring electrodes E1 and E8. However, this is just one example of a lead 33 having split-ring electrodes. In other designs, all electrodes can be split-ring, or there could be different numbers of split-ring electrodes at each longitudinal position (i.e., more or less than three), or the ring and split-ring electrodes could occur at different or random longitudinal positions, etc.

Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec).

In a SCS application, as is useful to alleviate chronic back pain for example, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In a DBS application, as is useful in the treatment of tremor in Parkinson's disease for example, the IPG 10 is typically implanted under the patient's clavicle (collarbone). Percutaneous leads 15 are tunneled through the neck and the scalp where the electrodes 16 are implanted through holes drilled in the skull and positioned for example in the subthalamic nucleus (STN) and the pedunculopontine nucleus (PPN) in each brain hemisphere. In other IPG examples designed for implantation directly at a site requiring stimulation, the IPG can be lead-less, having electrodes 16 instead appearing on the body of the IPG 10. The IPG lead(s) can be integrated with and permanently connected to the IPG 10 in other solutions.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1A, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth™, Zigbee™, WiFi, MICS, and the like.

Stimulation in IPG 10 is typically provided by pulses each of which may include a number of phases such as 30a and 30b, as shown in the example of FIG. 2A. In the example shown, such stimulation is monopolar, meaning that a current is provided between at least one selected lead-based electrode (e.g., E1) and the case electrode Ec 12. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30a), and thus provides pulses which sink a negative current of amplitude −I from the tissue. The case electrode Ec has been selected as an anode (again during first phase 30a), and thus provides pulses which source a corresponding positive current of amplitude +I from the tissue. Note that at any time the current sunk from the tissue (e.g., −I at E1 during phase 30a) equals the current sourced to the tissue (e.g., +I at Ec during phase 30a) to ensure that the net current injected into the tissue is zero. The polarity of the currents at these electrodes can be changed: Ec can be selected as a cathode, and E1 can be selected as an anode, etc.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current through a patient's tissue, R, hopefully with good therapeutic effect. In the example shown, and consistent with the first pulse phase 30a of FIG. 2A, electrode E1 has been selected as a cathode electrode to sink current from the tissue R and case electrode Ec has been selected as an anode electrode to source current to the tissue R. Thus PDAC $40_C$ and NDAC $42_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30a, charge will build up across the DC-blockings capacitors C1 and Cc associated with the electrodes E1 and Ec used to produce the current, giving rise to voltages Vc1 and Vcc which decrease in accordance with the amplitude of the current and the capacitance of the capacitors 38 (dV/dt=I/C). During the second pulse phase 30b, when the polarity of the current I is reversed at the selected electrodes E1 and Ec, the stored charge on capacitors C1 and Cc is actively recovered, and thus voltages Vc1 and Vcc increase and return to 0V at the end the second pulse phase 30b.

To recover all charge by the end of the second pulse phase 30b of each pulse (Vc1=Vcc=0V), the first and second phases 30a and 30b are charged balanced at each electrode, with the first pulse phase 30a providing a charge of −Q (−I*PW) and the second pulse phase 30b providing a charge of +Q (+I*PW) at electrode E1, and with the first pulse phase 30a providing a charge of +Q and the second pulse phase 30b providing a charge of −Q at the case electrode Ec. In the example shown, such charge balancing is achieved by using the same pulse width (PW) and the same amplitude (|I|) for each of the opposite-polarity pulse phases 30a and 30b. However, the pulse phases 30a and 30b may also be charged balance at each electrode if the product of the amplitude and pulse widths of the two phases 30a and 30b are equal, or if the area under each of the phases is equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes ei 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced.

Therefore, and as shown in FIG. 2A, passive charge recovery typically occurs after the issuance of second pulse phases 30b, for example during at least a portion 30c of the quiet periods between the pulses, by closing passive recovery switches $41_i$. As shown in FIG. 3, the other end of the switches $41_i$ not coupled to the electrode nodes ei 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30a or 30b have a predominance of charge at a given electrode.

Passive charge recovery 30c may alleviate the need to use biphasic pulses for charge recovery, especially in the DBS context when the amplitudes of currents may be lower, and therefore charge recovery less of a concern. For example, and although not shown in FIG. 2A, the pulses provided to the tissue may be monophasic, comprising only a first pulse phase 30a. This may be followed thereafter by passive charge recovery 30c to eliminate any charge build up that occurred during the singular pulses 30a.

FIG. 4 shows an external trial stimulation environment that may precede implantation of an IPG 10 in a patient, particularly in an SCS application. During external trial stimulation, stimulation can be tried on a prospective implant patient without going so far as to implant the IPG 10. Instead, one or more trial electrode arrays 17' (e.g., one or more trial percutaneous leads 15/33 or trial paddle leads 19) are implanted in the patient's tissue at a target location 52, such as within the spinal column or the brain as explained earlier. The proximal ends of the trial electrode array(s) 17' exit an incision 54 in the patient's tissue and are connected to an External Trial Stimulator (ETS) 50. The ETS 50 generally mimics operation of the IPG 10, and thus can provide stimulation to the patient's tissue as explained above. See, e.g., U.S. Pat. No. 9,259,574, disclosing a design for an ETS. The ETS 50 is generally worn externally by the patient for a short while (e.g., two weeks), which allows the patient and his clinician to experiment with different stimulation parameters to hopefully find a stimulation program that alleviates the patient's symptoms. If external trial stimulation proves successful, the trial electrode array(s) 17' are explanted, and a full IPG 10 and a permanent electrode array 17 (e.g., one or more percutaneous 15/33 or paddle 19 leads) are implanted as described above; if unsuccessful, the trial electrode array(s) 17' are simply explanted.

Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50 may also include stimulation circuitry able to form stimulation in accordance with a stimulation program, which circuitry may be similar to or comprise the same stimulation circuitry 28 (FIG. 3) present in the IPG 10. ETS 50 may also include a battery (not shown) for operational power.

FIG. 5 shows various external devices that can wirelessly communicate data with the IPG 10 or ETS 50, including a patient, hand-held external controller 60, and a clinician programmer 70. Both of devices 60 and 70 can be used to wirelessly transmit a stimulation program to the IPG 10 or ETS 50—that is, to program their stimulation circuitries to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64a capable of wirelessly communicating with the coil antenna 27a or 56a in the IPG 10 or ETS 50. The external controller 60 can also have a far-field RF antenna 64b capable of wirelessly communicating with the RF antenna 27b or 56b in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27a or 56a, wand 76 can likewise include a coil antenna 80a to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80b to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp. Such control circuitry 88, in addition to executing the clinician programmer software 84 and rendering the GUI 82, can also enable communications via antennas 80*a* or 80*b* to communicate stimulation parameters chosen through the GUI 82 to the patient's IPG 10.

The user interface of the external controller 60 may provide similar functionality because the external controller 60 can include the same hardware and software programming as the clinician programmer. For example, the external controller 60 includes control circuitry 66 similar to the control circuitry 88 in the clinician programmer 70, and may similarly be programmed with external controller software stored in device memory.

SUMMARY

A system is disclosed comprising an implantable stimulator device and an external device configured to communicate with the implantable stimulator device. The an implantable stimulator device, can comprise: a plurality of electrode nodes, each electrode node configured to be coupled to one of a plurality of electrodes configured to contact a patient's tissue, and first control circuitry configured to execute an algorithm configured to provide at least one test current between at least two of the electrodes nodes, and in response to the at least one test current measure a voltage data set at at least some of the plurality of electrode nodes. The external device can comprise: second control circuitry configured to render a graphical user interface, wherein the graphical user interface comprises a first input to cause the first control circuitry in the implantable stimulator device to execute the algorithm, receive the voltage data set from the implantable stimulator device, and determine a representation of an electric field in the patient's tissue using the received voltage data set and using potential stimulation parameters for the patient.

The external device can be further configured to transmit the potential stimulation parameters to the implantable stimulator device for execution. The potential stimulation parameters may comprise at least selected ones of the plurality of electrodes, and an amplitude of a current to be provided at each selected electrode. The graphical user interface may comprises at least one input to allow a user to enter the potential stimulation parameters.

The second control circuitry may further be configured to render the representation of the electric field as an electric field image, and to display in the graphical user interface the electric field image superimposed on a lead image showing the plurality of electrodes. The second control circuitry may be further configured to receive a tissue image, and to display the tissue image on the graphical user interface in relation to the electric field and lead images. The graphical user interface may comprises one or more inputs to allow a user to adjust a view of the displayed tissue image, electric field image, and lead image. The determined representation of the electric field may be three-dimensional. The second control circuitry may be configured to define positions in three-dimensional space relative to the plurality of electrodes, and uses the received voltage data set to determine a plurality of resistances between neighboring ones of the positions. The second control circuitry may be configured to determine the representation of the electric field by determining voltages at the positions in response to the potential stimulation parameters.

The voltage data set may be measured during the at least one test current. The algorithm may be configured to provide a test current between different combinations of at least two of the electrodes nodes, and wherein the voltage data set is measured during each of the test currents. The voltage data set may comprise a plurality of single ended voltage measurement taken with respect to a reference potential at the at least some of the electrodes nodes. The voltage data set may comprise a plurality of voltage differential measurements taken between different combinations of the at least some of the electrodes nodes. The test current may comprise current pulses. The current pulses may comprise biphasic current pulses.

The implantable stimulator device may further comprise a case for housing the first control circuitry, wherein a conductive portion of the case comprises one of the plurality of electrodes. The implantable stimulator device may further comprise one or more implantable leads comprising the plurality of electrodes. The stimulator device may comprise a fully-implantable pulse generator. The stimulator device may comprises an external trial stimulator.

An external device is disclosed that is configured to communicate with a stimulator device having a plurality of electrode nodes, each electrode node configured to be coupled to one of a plurality of electrodes configured to contact a patient's tissue. The external device may comprise: control circuitry configured to render a graphical user interface, wherein the graphical user interface is configured to receive a user input to cause the stimulator device to execute an algorithm in which at least one test current is applied between at least two of the electrodes nodes, receive from the stimulator device a voltage data set at at least some of the plurality of electrode nodes measured during the provision of the at least one test current, receive from a database information indicative of the three-dimensional position of the plurality of electrodes, receive potential stimulation parameters to be executed within the stimulator device, and determine from the information, the voltages data set, and the potential stimulation parameters a representation of an electric field in the patient's tissue.

The external device may be further configured to transmit the potential stimulation parameters to the implantable stimulator device for execution. The potential stimulation parameters may comprise at least selected ones of the plurality of electrodes, and an amplitude of a current to be provided at each selected electrode. The graphical user interface may comprise at least one input to allow a user to enter the potential stimulation parameters.

The control circuitry may be further configured to render the representation of the electric field as an electric field image, and to display in the graphical user interface the electric field image superimposed on a lead image showing the plurality of electrodes. The control circuitry may be further configured to receive a tissue image, and to display the tissue image on the graphical user interface in relation to the electric field and lead images. The graphical user interface may comprise one or more inputs to allow a user to adjust a view of the displayed tissue image, electric field image, and lead image.

The determined representation of the electric field may be three-dimensional. The control circuitry may be configured to define positions in three-dimensional space relative to the plurality of electrodes, and uses the received voltage data set to determine a plurality of resistances between neighboring ones of the positions. The control circuitry may be configured to determine the representation of the electric field by determining voltages at the positions in response to the potential stimulation parameters.

The algorithm may be configured to provide a test current between different combinations of at least two of the electrodes nodes, and wherein the voltage data set is measured during each of the test currents. The voltage data set may comprise a plurality of single ended voltage measurement taken with respect to a reference potential at the at least some of the electrodes nodes. The voltage data set may comprise a plurality of voltage differential measurements taken between different combinations of the at least some of the electrodes nodes. The test current may comprise current pulses. The current pulses may comprise biphasic current pulses.

A non-transitory computer readable media is disclosed including instruction executable on an external device, wherein the external device is configured to communicate with a stimulator device having a plurality of electrode nodes, each electrode node configured to be coupled to one of a plurality of electrodes configured to contact a patient's tissue, wherein the instructions when executed may be configured to: render a graphical user interface, wherein the graphical user interface is configured to receive a user input to cause the stimulator device to execute an algorithm in which at least one test current is applied between at least two of the electrodes nodes; receive from the stimulator device a voltage data set at at least some of the plurality of electrode nodes measured during the provision of the at least one test current; receive from a database information indicative of the three-dimensional position of the plurality of electrodes; receive potential stimulation parameters to be executed within the stimulator device; and determine from the information, the voltages data set, and the potential stimulation parameters a representation of an electric field in the patient's tissue.

BRIEF DESCRIPTION OF THE DRAWINGS

FIGS. 2A and 2B show an example of stimulation pulses (waveforms) producible by the IPG or by an External Trial Stimulator (ETS), in accordance with the prior art.

FIG. 3 shows an example of stimulation circuitry useable in the IPG or ETS, in accordance with the prior art.

In FIG. 7 it is assumed that the electric field is determined using a bulk tissue resistance.

FIG. 10A shows the timing of the voltage differential measurements in relation to the test current, while

In FIG. 11 the electric field is determined using the voltage differential data set rather than a bulk tissue resistance.

FIGS. 14A-14C show an alternative of the disclosed technique in which single ended voltage measurements are made at the electrodes rather than voltage differential measurements between different electrodes.

DETAILED DESCRIPTION

Figure 5:
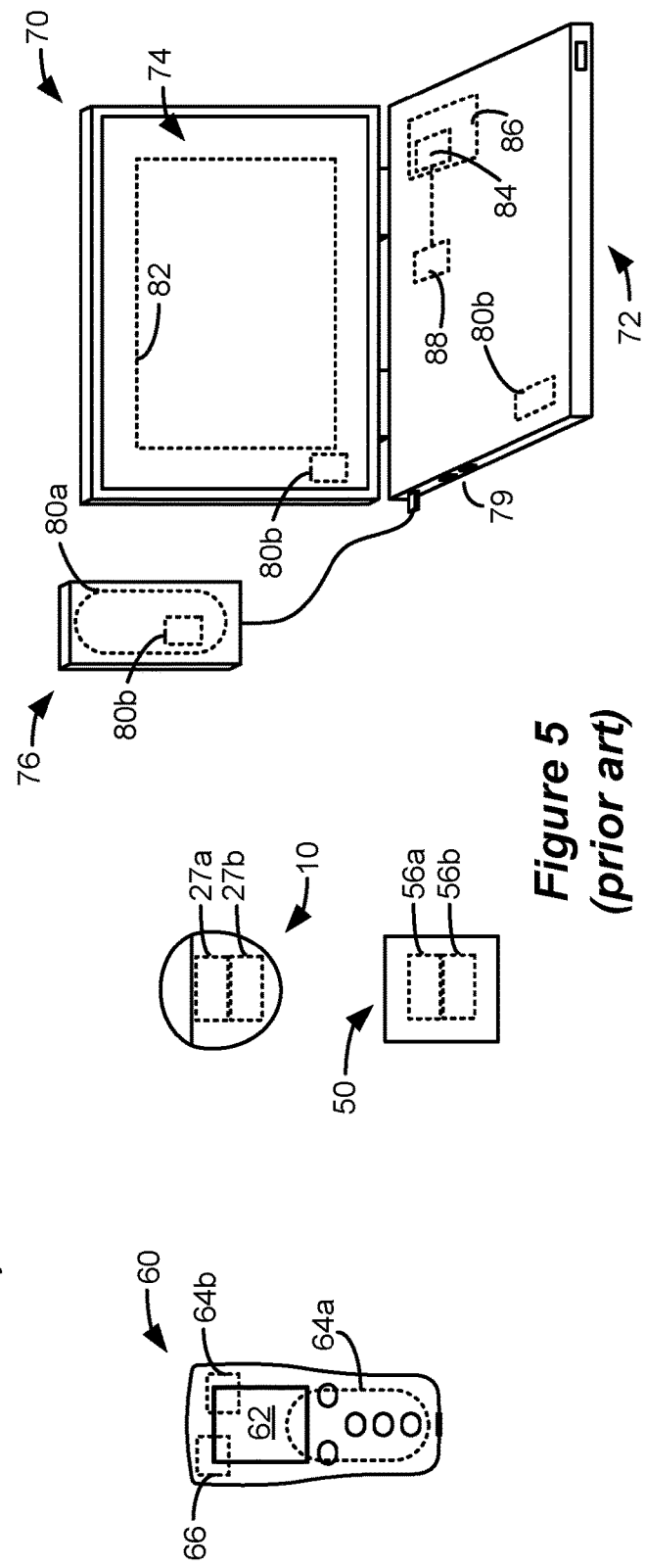
FIG. 5 shows various external devices capable of communicating with and programming stimulation in an IPG or ETS, in accordance with the prior art.
Figure 6:
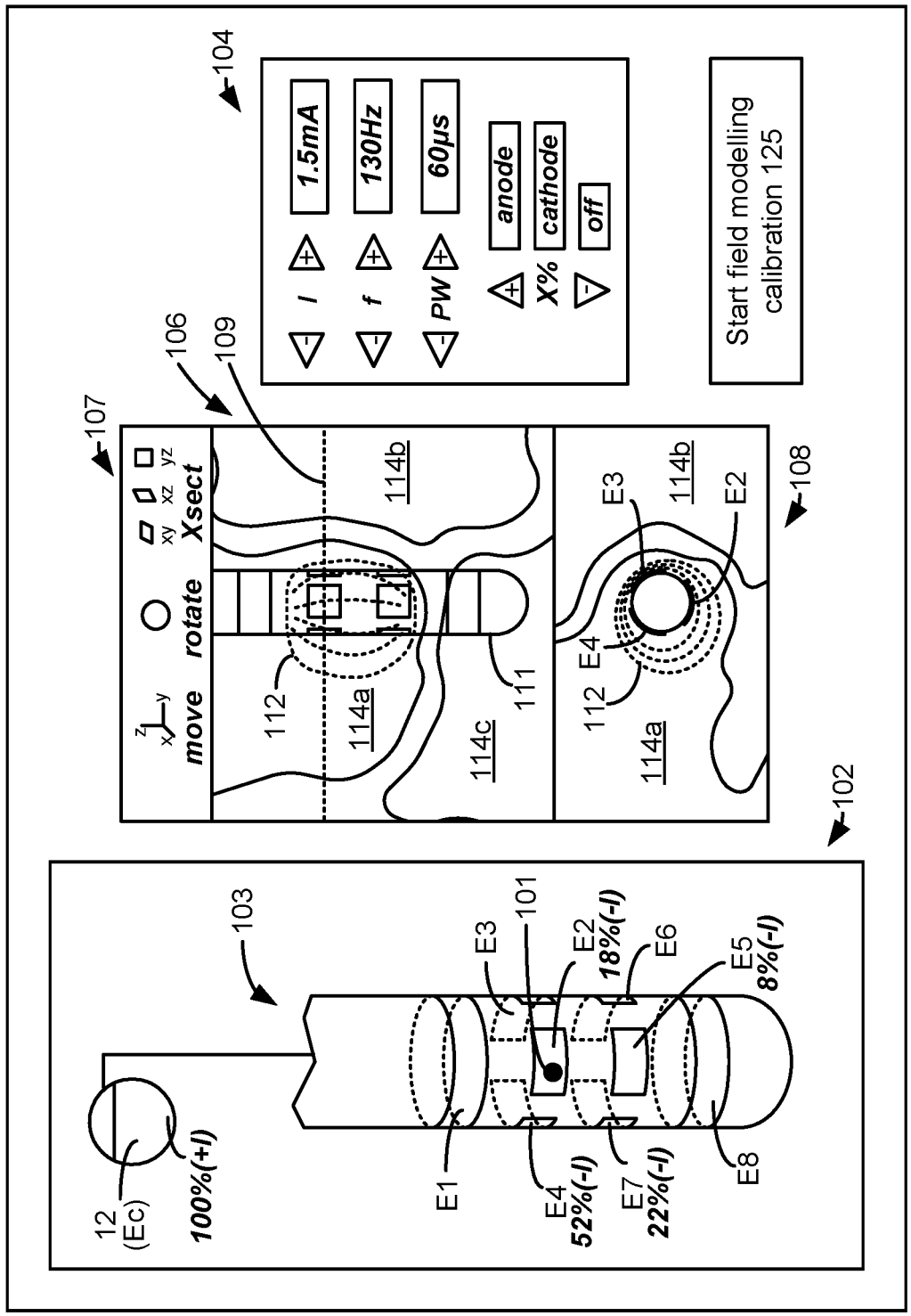
FIG. 6 shows a Graphical User Interface (GUI) operable on an external device such as a clinician programmer, which is capable of programming a stimulation program for the IPG or ETS, and which is also useable to view an electric field resulting from the stimulation program in the context of tissue structures in which electrodes are implanted.

Particularly in the DBS context, it can be useful to provide a clinician with a visual indication of how stimulation selected for a patient will interact with the tissue in which the electrodes are implanted. This is illustrated in FIG. 6, which shows a Graphical User Interface (GUI) 100 operable on an external device capable of communicating with an IPG 110 or ETS 150. Typically, and as assumed in the description that follows, GUI 100 would be rendered on a clinician programmer 70 (FIG. 5), which may be used during surgical implantation of the IPG 110 or the leads in an ETS 150, or after implantation when a therapeutically useful stimulation program is being chosen for a patient. However, GUI 100 could be rendered on a patient external programmer 60 (FIG. 5) or any other external device capable of communicating with the IPG 110 or ETS 150.

GUI 100 allows a clinician (or patient) to select the stimulation program that the IPG 110 or ETS 150 will provide. In this regard, the GUI 100 may include a stimulation parameter interface 104 where various aspects of the stimulation program can be selected or adjusted. For example, interface 104 allows a user to select the amplitude (e.g., a current I) for stimulation; the frequency (f) of stimulation pulses; and the pulse width (PW) of the stimulation pulses. Stimulation parameter interface 104 can be significantly more complicated, particularly if the IPG 100 or ETS 150 supports the provision of stimulation that is more complicated than a repeating sequence of pulses. See, e.g., U.S. Patent Application Publication 2018/0071513. Nonetheless, interface 104 is simply shown for simplicity in FIG. 6 as allowing only for amplitude, frequency, and pulse width adjustment. Stimulation parameter interface 104 may include inputs to allow a user to select whether stimulation will be provided using biphasic (FIG. 2A) or monophasic pulses, and to select whether passive charge recovery will be used, although again these details aren't shown for simplicity.

Stimulation parameter interface 104 may further allow a user to select the active electrodes—i.e., the electrodes that will receive the prescribed pulses. Selection of the active electrodes can occur in conjunction with a leads interface 102, which can include an image 103 of the one or more leads that have been implanted in the patient. Although not shown, the leads interface 102 can include a selection to access a library of relevant images 103 of the types of leads that may be implanted in different patients.

Figure 1A:
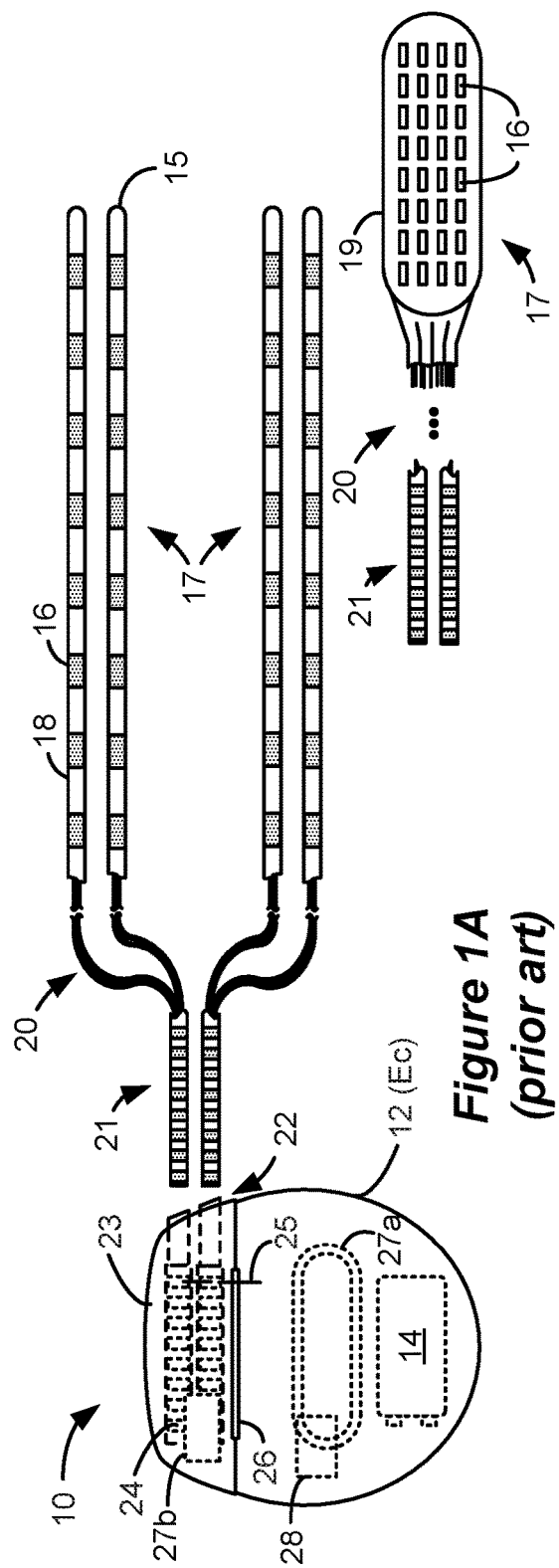
FIG. 1A shows an Implantable Pulse Generator (IPG), in accordance with the prior art.
Figure 1B:
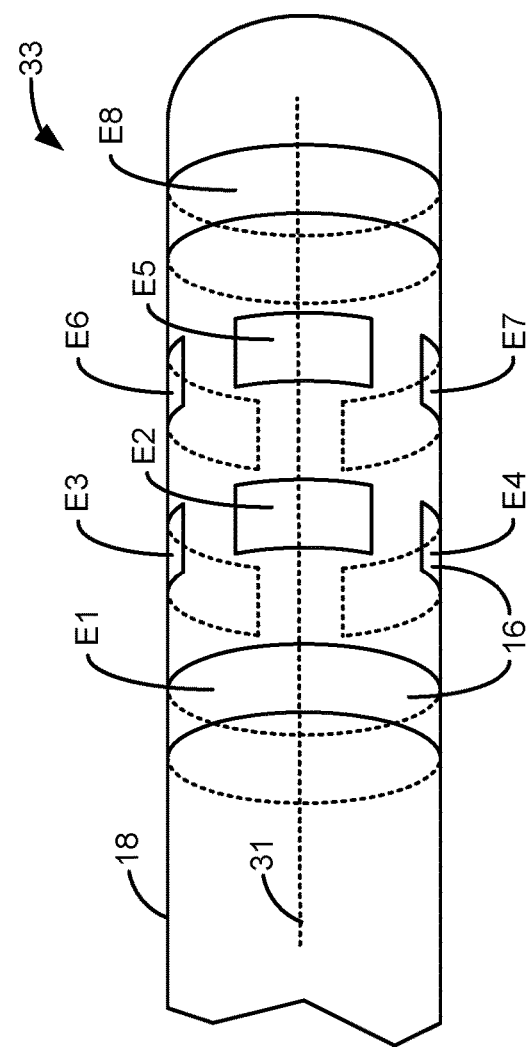
FIG. 1B shows a percutaneous lead having split-ring electrodes, in accordance with the prior art.
Figure 4:
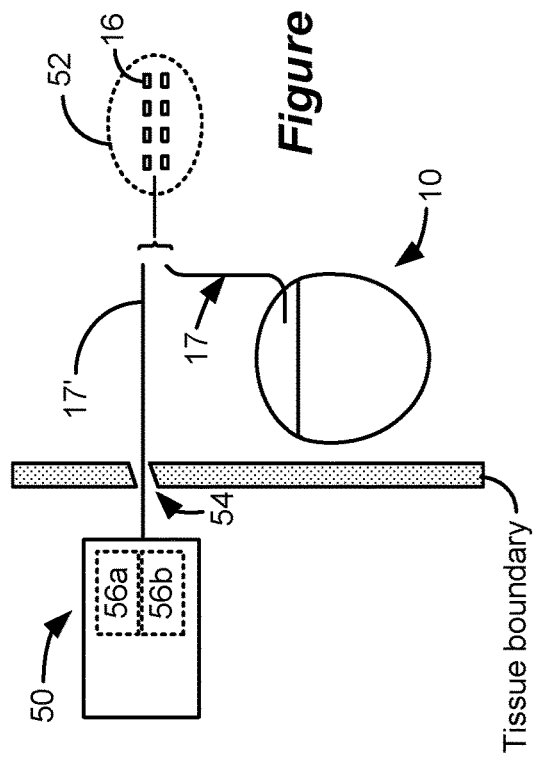
FIG. 4 shows an ETS environment useable to provide stimulation before implantation of an IPG, in accordance with the prior art.

In the example shown in FIG. 6, the leads interface 102 shows an image 103 of a single split-ring lead similar to that described earlier with respect to FIG. 1B. The leads interface 102 can include a cursor 101 that the user can move (e.g., using a mouse connected to the clinician programmer 70) to select an illustrated electrode 16 (e.g., E1-E8, or the case electrode Ec). Once an electrode has been selected, the stimulation parameter interface 104 can be used to designate the selected electrode as an anode that will source current to the tissue, or as a cathode that will sink current from the tissue. Further, the stimulation parameter interface 104 allows the amount of the total anodic or cathodic current +I or −I that each selected electrode will receive to be specified in terms of a percentage, X. For example, in FIG. 6, the case electrode 12 Ec is specified to receive X=100% of the current I as an anodic current +I. The corresponding cathodic current −I is split between electrodes E2 (0.18*−I), E4 (0.52*−I), E5 (0.08*−I), and E7 (0.22*−I). Thus, two or more electrodes can be chosen to act as anodes or cathodes at a given time, allowing the electric field in the tissue to be shaped, as explained further below. The currents so specified at the selected electrodes can be those provided during a first pulse phase (if biphasic pulses are used), or during an only pulse phase (if monophasic pulses are used).

GUI 100 can further include a visualization interface 106 that can allow a user to view an electric field image 112 formed on the one or more leads given the selected stimulation parameters. The electric field image 112 is formed by field modelling in the clinician programmer 70, as discussed further below. Only one lead is shown in the visualization interface 106 for simplicity, although again a given patient might be implanted with more than one lead. Visualization interface 106 provides an image 111 of the lead(s) which may be three-dimensional.

The visualization interface 106 preferably, but not necessarily, further includes tissue imaging information 114 taken from the patient, represented as three different tissue structures 114a, 114b and 114c in FIG. 6 for the patient in question, which tissue structures may comprise different areas of the brain for example. Such tissue imaging information may comprise a Magnetic Resonance Image (MM), a Computed Tomography (CT) image or other type of image, and is preferably taken prior to implantation of the lead(s) in the patient. Often, one or more images, such as an MRI, CT, and/or a brain atlas are scaled and combined in a single image model. As one skilled in the art will understand, the location of the lead(s) can be precisely referenced to the tissue structures 114i because the lead(s) are implanted using a stereotactic frame (not shown). This allows the clinician programmer 70 on which GUI 100 is rendered to overlay the lead image 111 and the electric field image 112 with the tissue imaging information in the visualization interface 106 so that the position of the electric field 112 relative to the various tissue structures 114i can be visualized. The image of the patient's tissue may also be taken after implantation of the lead(s), or tissue imaging information may comprise a generic image pulled from a library which is not specific to the patient in question.

The various images shown in the visualization interface 106 (i.e., the lead image 111, the electric field image 112, and the tissue structures 114i) can be three-dimensional in nature, and hence may be rendered in the visualization interface 106 in a manner to allow such three-dimensionality to be better appreciated by the user, such as by shading or coloring the images, etc. Additionally, a view adjustment interface 107 may allow the user to move or rotate the images, using cursor 101 for example.

GUI 100 can further include a cross-section interface 108 to allow the various images to be seen in a two-dimensional cross section. Specifically, cross-section interface 108 shows a particular cross section 109 taken perpendicularly to the lead image 111 and through split-ring electrodes E2, E3, and E4. This cross section 109 can also be shown in the visualization interface 106, and the view adjustment interface 107 can include controls to allow the user to specify the plane of the cross section 109 (e.g., in XY, XZ, or YZ planes) and to move its location in the image. Once the location and orientation of the cross section 109 is defined, the cross-section interface 108 can show additional details. For example, the electric field image 112 can show equipotential lines allowing the user to get a sense of the strength and reach of the electric field at different locations.

Although GUI 100 includes stimulation definition (102, 104) and imaging (108, 106) in a single screen of the GUI, these aspects can also be separated as part of the GUI 100 and made accessible through various menu selections, etc.

GUI 100 is particularly useful because it allows the electric field as reflected in electric field image 112 to be seen relative to surrounding tissue structures 114i. This allows the user to adjust the stimulation parameters to recruit, or avoid recruiting, particular tissue structures 114i. Assume for example that it is desirable for a given patient to stimulate tissue structure 114a, but to not stimulate tissue structures 114b or 114c. This may be because tissue structure 114a is causing undesired patient symptoms (e.g., tremor) that stimulation can alleviate, while stimulation of tissue structures 114b and 114c will cause undesired side effects. The clinician can then use GUI 100 to adjust stimulation (e.g., adjust the amplitude I, select new electrodes for stimulation, or adjust the percentage X % of amplitude I that each selected electrode receives) to steer the electric field to a proper tissue location. In the example shown, and as best seen in the cross-section interface 108, higher cathodic currents are provided at split-ring electrodes E4 (0.52*−I) and E2 (0.18*−I) because these electrodes are generally speaking facing towards tissue structure 114a and away from tissue structure 114b. By contrast, split-ring electrode E3 carries no cathodic current because it generally faces towards tissue structure 114b. The result is an electric field 112 that is more predominant in tissue structure 114a and less predominant in tissue structure 114b. To summarize, GUI 100 is useful in allowing the clinician to visualize via the electric field image 112 where stimulation will occur, and preferably in relation to surround tissue structures. Further, GUI 100 allows stimulation to be adjusted and to visualize how such adjustments will change the shape and location of the electric field.

Figure 7:
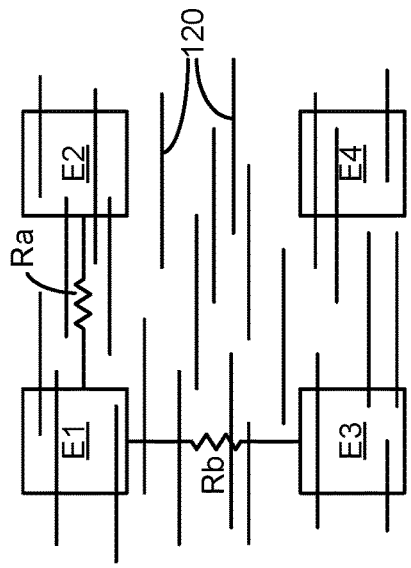
FIG. 7 shows a field modelling algorithm and related circuitry operable in an external device such as a clinician programmer to determine an electric field based on a stimulation program selected for the patient.

FIG. 7 shows how the electric field, and its corresponding image 112, can be determined for a particular stimulation program. Preferably, the electric field image 112 is formed by field modelling in the control circuitry 88 within the clinician programmer 70, although again another external device such as the patient external controller 60 could also be used. Field modelling occurs using a field modelling algorithm 116 operating within the control circuitry, for example as a firmware program.

The field modelling algorithm 116 receives relevant stimulation parameters from the stimulation program that were entered via the external device's GUI 100. At a minimum, such relevant parameters include the electrodes selected for stimulation (Es), and the amplitude (Is) (e.g., current) at each selected electrodes. Again, the amplitudes can be positive or negative, depending whether the selected electrodes are to act as anodes or cathodes. Other stimulation parameters may be provided to the field modelling algorithm 116 such as pulse width or frequency, but these may be of less relevance as they deal with stimulation timing rather than peak amplitude as occurs during a pulse for example. Note that these stimulation parameters such as Es and Is may comprise potential stimulation parameters that are to be modelled and displayed. These potential stimulation parameters may not actually be transmitted to the IPG 110 or ETS 150 for execution, particularly if their electric field image 112 does not seem suitable for the patient in light of tissue structures 114i. By contrast, if the rendered electric field image 112 seems suitable for the patient, the potential stimulation parameters may be transmitted to the IPG 110 or ETS 150 for execution to see how they work for the patient.

Further provided to the field modelling algorithm 116 is information relevant to the particular lead(s) chosen for stimulation, such as the size, location, and spacing of the electrodes 16 on the lead(s), which may be provided by a leads database 115. This allows the field modelling algorithm 116 to determine the physical size and shape of the electric field relative to the lead(s) and to the selected electrodes. If more than one lead is used to form an electrode array 17 (FIG. 1A), leads database 115 may also provide information relevant to the spacing and orientation of one lead to another, which may be determined in any number of manners.

Another parameter received by the field modelling algorithm 116 is the bulk resistance of the tissue, ρ. This is beneficial so that the algorithm 116 can estimate the voltage at different points in the tissue surrounding the electrodes, and hence the strength of the electric field at those points (E=dV/dx). Generally speaking, and assuming a current of a set amplitude flows through the tissue, a higher tissue resistance ρ will produce a greater voltage drop and a greater electric field, while a lower ρ will produce a lower voltage drop and a lower electric field. Buk tissue resistance ρ may be measured empirically or estimated based on the constituents of the tissue (salt water, fat, etc.).

Once the field modelling algorithm 116 has received the above-mention data, it can determine an electric field in the tissue in three-dimensional space, which can in be turn used to form the electric field image 112 that is provided to the GUI 100, and depicted in visualization and cross-section interfaces 106 and 108 (FIG. 6).

Figure 8:
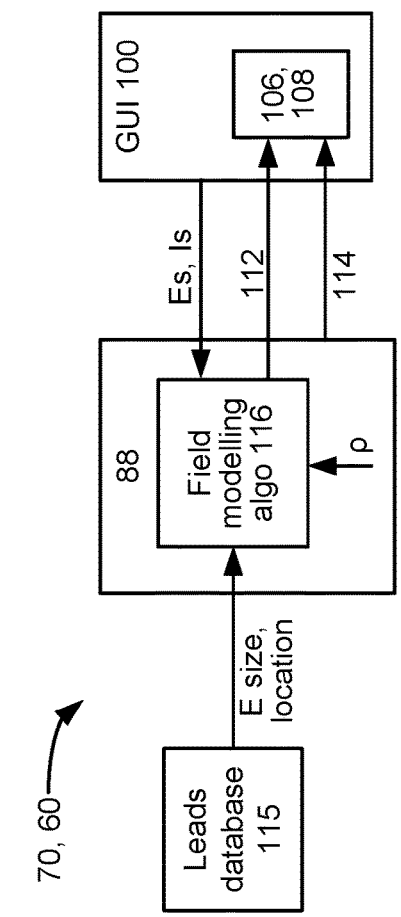
FIG. 8 shows linear neural fibers, and describes how this linearity can affect the directional resistance of neural tissue.

The inventor is concerned that a bulk tissue resistance ρ may not well model a given patient's tissue in all cases, thus causing the field modelling algorithm 116 to determine an electric field and render an electric field image 112 that may not be reflective of the particular tissue in which the leads are implanted. Use of a bulk tissue resistance ρ assumes that tissue is homogenous, and has equal resistance in all directions in three-dimensional space. This assumption may not be accurate, because the resistance of neural tissue can vary depending whether resistance is measured parallel or perpendicular to neural fibers. This is illustrated in FIG. 8, which shows four electrodes (E1-E4) arrayed in a two-dimensional square. These electrodes are implanted in neural tissue having neural fibers 120 which as shown are linear in nature. Experimentation teaches that the resistance Ra of the tissue taken parallel to the neural fibers 120, e.g., between electrodes E1 and E2, can be up to ten times lower than the resistance Rb of the tissue taken perpendicular to the neural fibers 120, e.g., between electrodes E1 and E3.

According to embodiments of the invention, a field measurement algorithm and measuring circuitry in the IPG or ETS, and an improved field modelling algorithm operable in an external device (e.g., a clinician programmer) in communication with the IPG or ETS, are used to determine an electric field in a patient's tissue, and to render an electric field image as may be shown in a Graphical User Interface (GUI) on the external device. In one example, the field measuring algorithm provides at least one test current between two electrodes, which produces voltages of particular magnitudes at the various electrodes. A plurality of voltage differentials are measured at different combinations of the electrodes during the provision of the at least one test current to create a voltage differential data set. This data set is then preferably wirelessly telemetered to the external device, where it is used by the improved field modelling algorithm. Preferably, the improved field modelling algorithm uses the voltage differential data instead of a bulk tissue resistance to model the electric field in the tissue. This allows the improved field modelling algorithm to determine directional resistances at different locations in the patient's tissue which, unlike a bulk tissue resistance, contains information concerning how resistivity in the patient's tissue may vary at different locations and in different directions. The improved field modelling algorithm can then use the stimulation program selected for the patient and the determined directional resistances to determine voltages in the patient's tissue at various locations, which in turn can be used to model a more-accurate electric field in the tissue, and preferably to render a more-accurate electric field image for display in the GUI.

Figure 9:
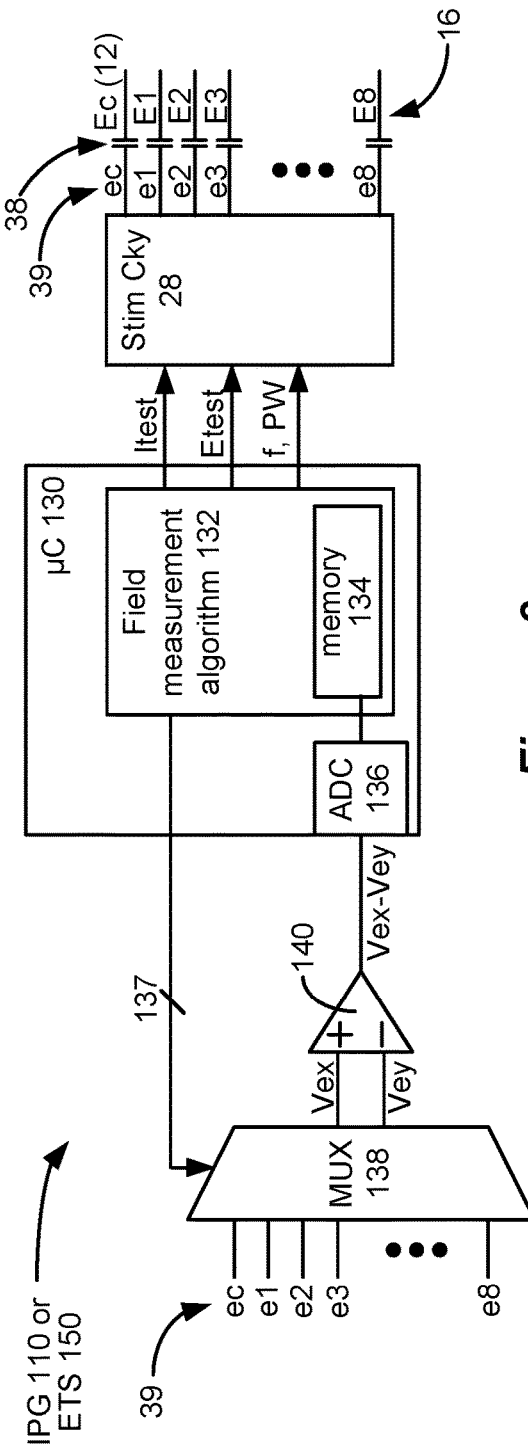
FIG. 9 shows a field measurement algorithm and related circuitry in an IPG or ETS that can be used to measure a voltage differential at various electrodes combinations in response to a test current issued between at least two of the electrodes.

The field measurement algorithm 132 and accompanying measuring circuitry in the IPG 110 or ETS 150 is shown in FIG. 9. Central to the IPG 110 or ETS 150 is control circuitry 130, which in one example can comprise a microcontroller, such as Part Number MSP430, manufactured by Texas Instruments. The control circuitry 130 more generally can comprise a microprocessor, Field Programmable Grid Array, Programmable Logic Device, Digital Signal Processor or like devices. Control circuitry 130 may include a central processing unit capable of executing instructions, with such instructions stored in volatile or non-volatile memory within or associated with the control circuitry. Control circuitry 130 may also include, operate in conjunction with, or be embedded within an Application Specific Integrated Circuit (ASIC), such as described in U.S. Patent Application Publications 2008/0319497, 2012/0095529, 2018/0071513, or 2018/0071520. The control circuitry 130 may comprise an integrated circuit with a monocrystalline substrate, or may comprise any number of such integrated circuits operating as a system. Control circuitry may also be included as part of a System-on-Chip (SoC) or a System-on-Module (SoM) which may incorporate memory devices and other digital interfaces. Stimulation circuitry 28 (FIG. 3) may comprise a portion of the control circuitry 130 as may measurement circuitry discussed further below.

Figure 10A:
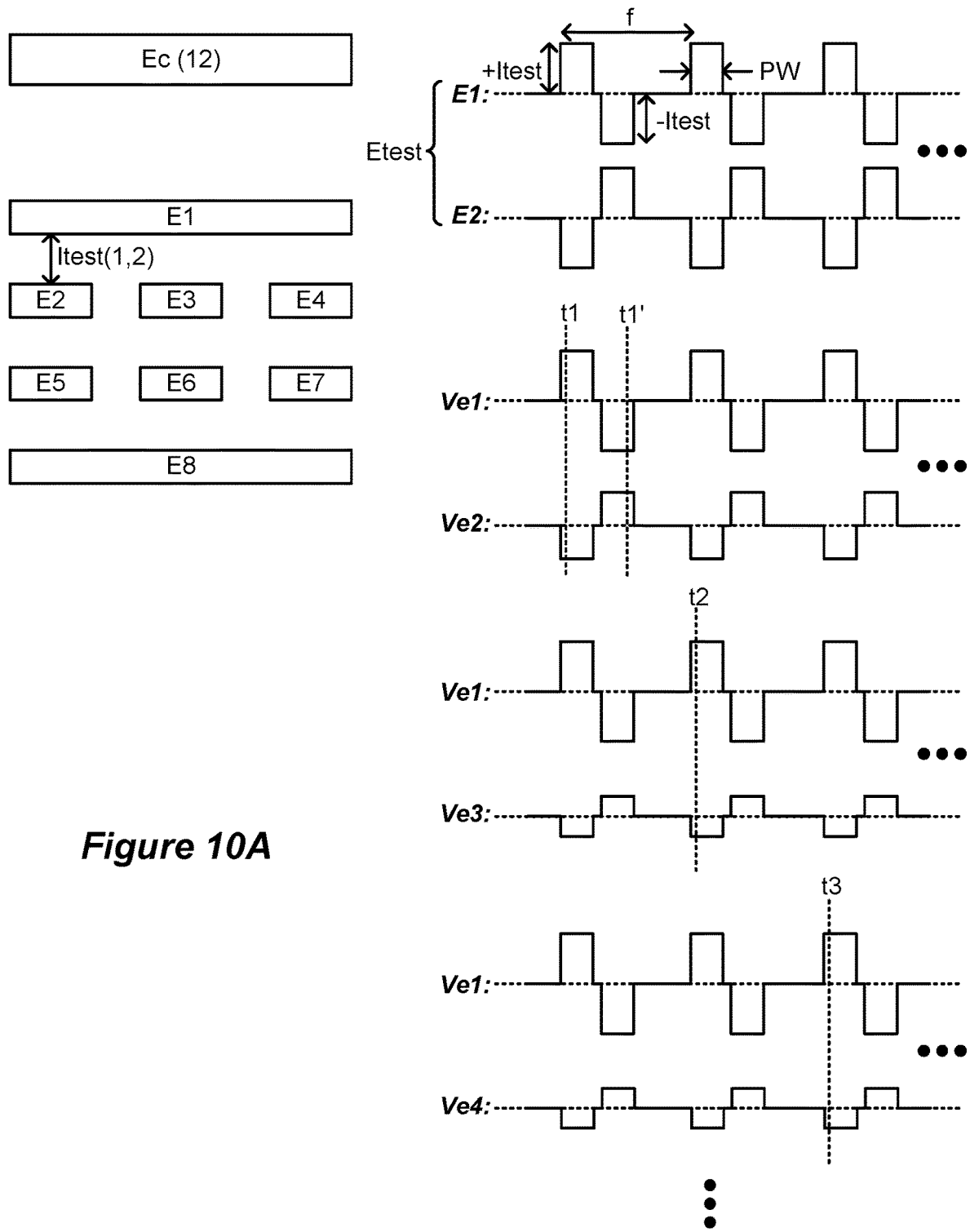

Control circuitry 130 includes the field measurement algorithm 132, which may comprise a firmware program downloaded to the IPG 110 or ETS 150 via an external device or during its manufacture. As will be described in further detail below, the field measurement algorithm 132 can start a test whereby a test current Itest is provided to at least two selected electrodes Etest. Itest is preferably formed as pulses, such as biphasic pulses as shown in FIG. 10A. The Itest pulses may however also be monophasic, and whether biphasic or monophasic the Itest pulses may be followed by passive charge recovery as described earlier. There are at least two selected electrodes Etest, because at least one will act as an anode electrode to source +Itest to the tissue and the at least one other will act as a cathode to sink −Itest from the tissue. As shown in FIG. 9, Itest, the selected electrodes Etest, and the selected electrodes' polarities (anode or cathode) can be provided to the IPG or ETS's stimulation circuitry 28 as described earlier (FIG. 3), and with relevant timing information such as pulse frequency (f) and pulse width (PW). Itest may be provided to different combinations of selected electrodes Etest. That is, the selected electrodes Etest may change during the test, as explained further below.

At various times during the provision of the test current Itest to the selected electrodes Etest, measurement circuitry under control of the field measurement algorithm 132 will measure a voltage difference between different pairs of electrodes. In one example, and as shown in FIG. 9, such measurement circuitry can include a multiplexer 138 having inputs connected to the electrode nodes ei 39. One or more control signal 137 issued by the field measurement algorithm 132 will select two of the electrode nodes ex and ey, thus passing their voltages Vex and Vey to the inputs of a differential amplifier 140. This differential amplifier 140 will compute the difference between these voltages, Vex-Vey, and this value can be digitized via an Analog-to-Digital Converter (ADC) 136. The ADC 136 may comprise a separate component, or may comprise part of analog input circuitry of the control circuitry 130. The various values of Vex-Vey are stored in a memory 134 associated with the field measurement algorithm 132.

Differential voltage measurements Vex-Vey are particularly useful in the context of the disclosed invention, because they generally reflect the conductivity of the tissue between the electrodes Ex and Ey across which the differential is sensed. As explained further below in conjunction with a description of improved field modelling algorithm 160 (FIG. 11), such voltage differentials are useful to characterize the resistivity of the tissue in the vicinity of the electrodes, which may be different at various locations, and which may vary in accordance with the linearity of the neural fibers in the tissue (FIG. 8).

Figure 10B:
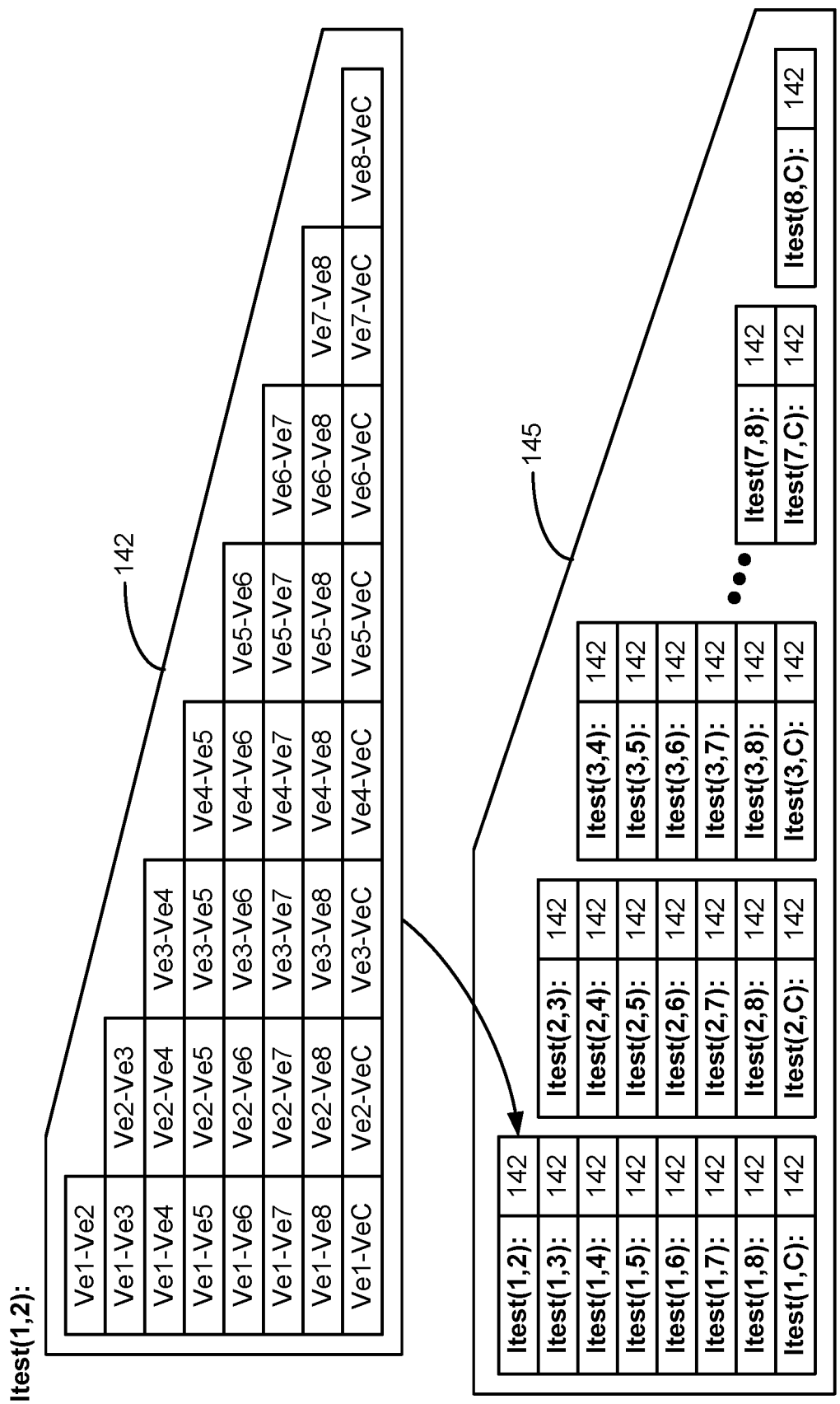
FIG. 10B shows the resulting voltage differential data set.

FIGS. 10A-10B illustrate an example of how field measurement algorithm 132 can operate the test to determine the various voltage differences between the electrodes. In FIG. 10A, Itest is provided between selected electrodes E1 and E2 (Itest(1,2)), preferably as biphasic pulses. Although not shown, passive charge recovery can follow issuance of the pulses to assist in charge recovery, as described earlier. The amplitude of Itest is preferably selected to be as low as possible, and preferably lower than might otherwise be needed to provide a therapeutic effect. Ideally, the amplitude of Itest will be low enough to not be noticeable by the patient, and Itest may be varied from patient to patient. Providing Itest between electrodes E1 and E2 will cause voltages Ve1 and Ve2 to form at their respective electrodes nodes 39 depending on the conductivity of the tissue between these electrodes, and will cause an electric field to be formed in the tissue. This electric field will couple to the other electrodes E3, E4, etc., thus forming voltages Ve3, Ve4, etc., at their respective electrode nodes.

Various combinations of voltage differences Vex−Vey are measured during the issuance of the Itest pulses. For example, during a first pulse, the voltage difference between electrodes E1 and E2 (Ve1−Ve2) can be measured (at t1) by appropriate control of control signals 137. Note that it may be beneficial to sense this voltage differential (t1) at the beginning of the pulse. This is because the DC-blocking capacitors C1 and C2 38 (FIG. 9) associated with electrodes E1 and E2 will not have significantly charged at the beginning of the pulse, and hence Ve1 and Ve2 at that point in time will generally equal the voltages at the electrodes E1 and E2, and hence in the tissue. The timing is of less concern when sensing voltages at electrodes that aren't actively being driven. For example, because no current flows into electrodes E3, E4, etc., and thus DC-blocking capacitors C3 and C4 won't charge, Ve3, Ve4, etc. will equal the voltage at the electrodes E3 and E4 throughout the entire pulse. Note that if a biphasic pulse is used for Itest, the same absolute voltage difference Ve1−Ve2 can be measured during the second phase of the pulse (t1'), with the two voltage differences at t1 and t1' being averaged for example. In this example, it may be beneficial to sense the voltage differential (t1') at the end of the second phase, because the DC-blocking capacitors C1 and C2 38 (FIG. 9) associated with electrodes E1 and E2 will have been significantly discharged back to zero, and thus Ve1 and Ve2 at that point in time will again generally equal the voltages at the electrodes E1 and E2 and hence in the tissue.

During a second pulse (t2), the voltage difference between electrodes E1 and E3 (Ve1−Ve3) can be measured. During a third pulse (t3), the voltage difference between electrodes E1 and E4 (Ve1−Ve4) can be measured, and so on until all combinations involving electrode E1 have been measured, including if desired the voltage difference between E1 and the case electrode Ec (Ve1−VeC). Note that voltage difference measurements for different electrode combinations don't need to be taken for each subsequent Itest pulse. For example, a single voltage difference (e.g., Ve1−Ve2) can be measured over several Itest pulses and averaged by the field measurement algorithm 132 to improve the accuracy of the measurement.

Eventually, and again under appropriate control of control signals 137, combinations involving electrode E2 can be measured (Ve2−Ve3, Ve2−Ve4, Ve2−Ve5, etc.), followed by combinations involving electrode E3 (Ve3−Ve4, Ve3−Ve5, Ve3−Ve6, etc.).

The resulting voltage difference measurements are shown in FIG. 10B as data set 142 for a particular Itest (Itest(1,2)). If desired, the same voltage difference combinations can be measured by applying the test current Itest between different electrodes. Thus, as shown in FIG. 10B, the same data set 142 can be measured when applying the test current between electrodes E1 and E3 (Itest(1,3)); and E1 and E4 (Itest(1,4)), etc., and if desired between E1 and Ec (Itest(1,C)). Eventually, the test current can be applied to combinations involving electrode E2, i.e., between electrodes E2 and E3 (Itest(2,3)); and E2 and E4 (Itest(2,4)), and so on until the test current has been applied between all possible electrode combinations, thus rending the voltage differential data set 145 as shown in FIG. 10B.

While FIG. 10B shows voltage differential data 145 indicative of all potential combinations—i.e., providing a test current Itest between all potential electrode combinations, and further measuring voltage differences Vex−Vey at all potential electrode combinations at each test current—the disclosed technique does not require each of these combination to be taken, and therefore voltage differential data 145 can comprise a smaller subset of this data. For example, Itest can be applied between less than all potential electrode combinations, or may only be applied between a single electrode combination. Further, for a particular Itest electrode combination, not all potential voltage differences combination need to be measured. The more data 145 that is taken by the field measurement algorithm 132 will improve the fidelity of the electric field as computed by the improved field modelling algorithm 160 (FIG. 11) discussed further below, but will also increase the amount of computation needed.

Figure 11:
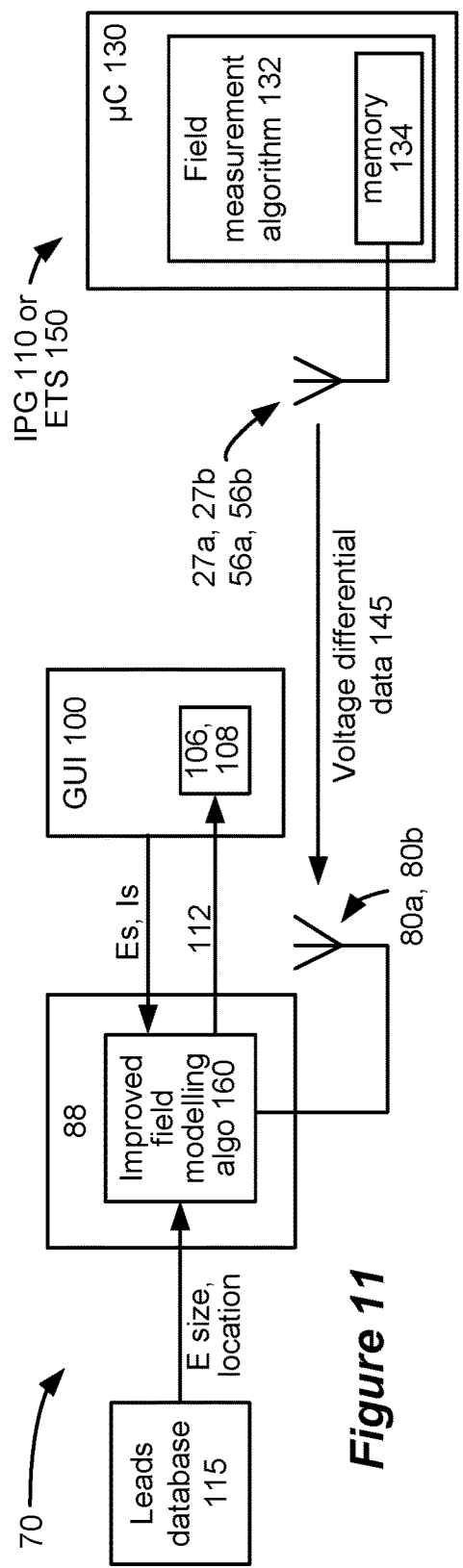
FIG. 11 shows an improved field modelling algorithm and related circuitry operable in an external device such as a clinician programmer to determine an electric field based on a stimulation program selected for the patient.

As shown in FIG. 11, the voltage differential data 145 taken in the IPG 110 or ETS 150 by the field measurement algorithm 132, once complete, is wirelessly telemetered to the external device (e.g., the clinician programmer 70) running the GUI 100, where it is processed by improved field modelling algorithm 160. This can involve use of the induction antennas 27a, 56a, and 80a, or the RF antennas 27b, 56b, and 80b described earlier. (If an ETS 150 is used, the voltage differential data 145 can also be provided to the clinician programmer by a cable). Alternatively, the field measurement algorithm 132 within the IPG 110 or ETS 150 can perform at least some of the functionality of the improved field modelling algorithm 160, and telemeter at least partial results to the clinician programmer 70 to ease computation at that portion of the system. However, because the improved field modelling algorithm 160 can be computationally intensive, it is preferred that such computation be fully off-loaded to the clinician programmer 70. This is also logical because the clinician programmer 70 can be used to view (via interfaces 106 and 108; FIG. 6) the electric field image 112 that the improved field modelling algorithm 160 produces. Improved field modelling algorithm 160 may be implemented similarly to the field modeling algorithm 116 described earlier (FIG. 7), and may comprise firmware operating within the control circuitry 88 of the clinician programmer or other external device. As explained further below (see FIG. 12), improved field modelling algorithm 160 can include a number of algorithms and databases, which are useful during a test procedure in which the patient's tissue is characterized, and which are useful to determine an electric field within the patient's tissue after such characterization and in light of a particular stimulation program chosen for the patient.

Figure 12:
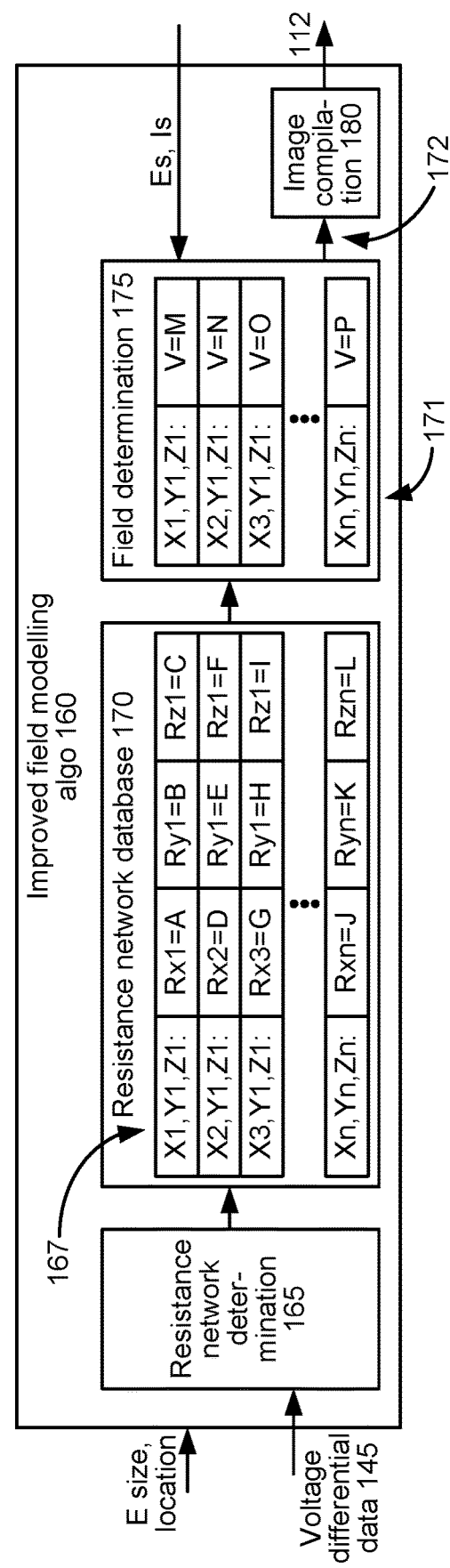
FIG. 12 shows further details of the improved field modelling algorithm, including determination of directional resistances during a test procedure to characterize a patient tissue, and use of the directional resistance to determine an electric field based on the stimulation program chosen for the patient.
Figure 13:
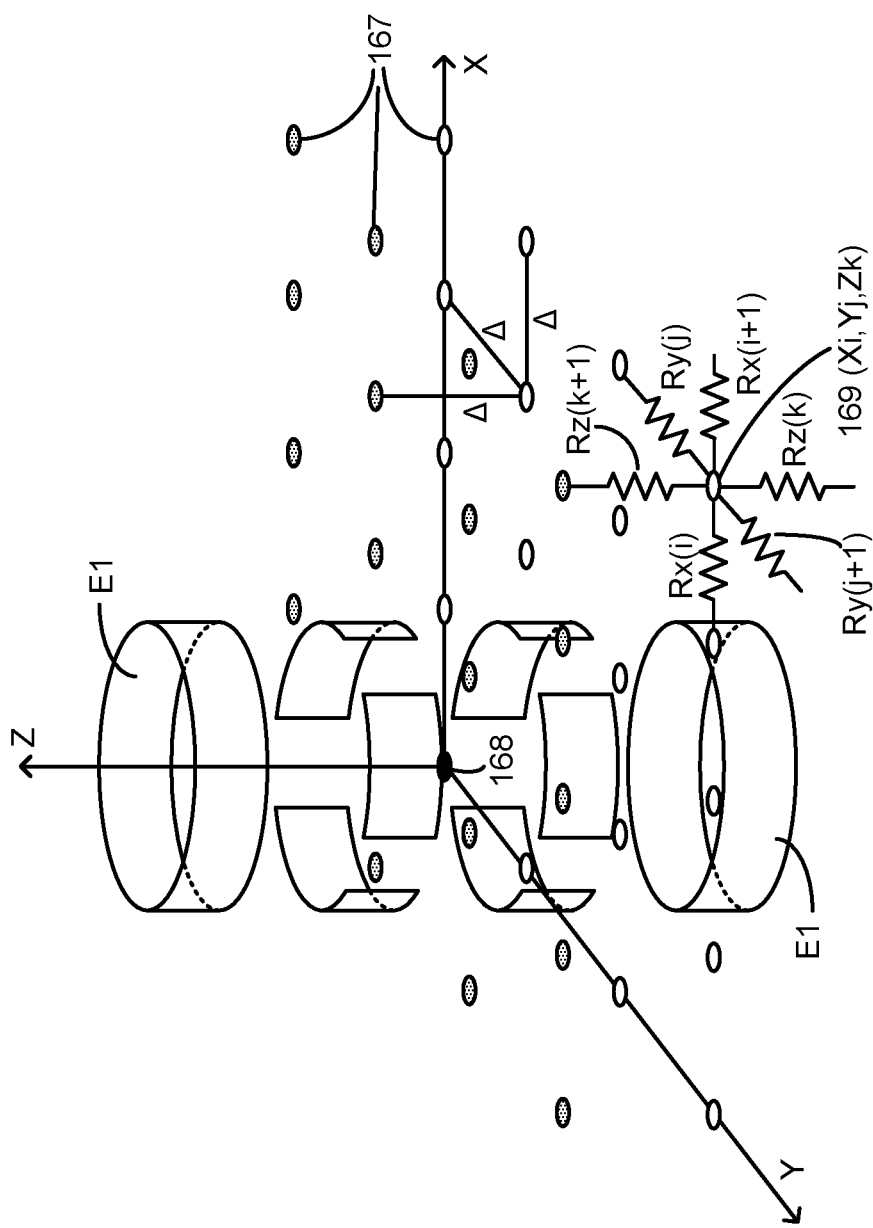
FIG. 13 shows how the improved field modelling algorithm can be used to define the directional resistances at various positions in a patient tissue.

Operation of the improved field modelling algorithm 160 is explained further with reference to FIGS. 12 and 13. Once the voltage differential data 145 is received at the improved field modelling algorithm 160, it is provided to a resistance network determination algorithm 165. Resistance network determination algorithm 165 can be configured in different manners, but in one example is used to determine directional resistances at different three-dimensional positions 167 in the tissue. These X, Y, Z positions 167 are shown in FIG. 13 relative to an XYZ grid, and relative to the positions of the split-ring electrodes of lead 33 described earlier (FIG. 1B). Again, the three-dimensional positioning of the electrodes—their size, location, and spacing—can be queried from the leads database 115 (FIG. 11), which preferably represent the electrodes as three-dimensional structures.

Positions 167 are defined by the improved field modelling algorithm 160 as being equally spaced (dimension Δ), although this isn't strictly necessary. Positions 167 are defined relative to an origin 168, which in this example is at the volumetric center of the electrodes (i.e., equidistant to split ring electrodes E2-E7; see FIG. 6), but this isn't necessary and the origin 168 can be defined elsewhere in the XYZ grid. For ease of illustration, positions 167 are only shown in one octant of the XYZ grid, but would in a practical application be defined in all octants. The number of positions 167 and their density (as determined by dimension Δ) can be variable. Having improved field modelling algorithm 160 consider a larger number of positions 167, or a greater density, would improve the fidelity of improved field modelling algorithm 160, but would be more computationally intensive. Because the improved field modelling algorithm 160 will eventually be used to compute a voltage at each of the positions 167 as useful in determining the electric field in the tissue, a point discussed further below, any positions 167 falling within the volume of the electrodes (i.e., positions that would be within the volume of the lead 33, and not within the tissue) can be ignored and are not illustrated in FIG. 13.

Resistance network determination algorithm 165 preferably determines a directional resistance from each of the positions 167. This is shown in FIG. 13 for a particular position 169 having coordinates Xi, Yj, and Zk. Preferably, a directional resistance is determined from position 169 to neighboring positions 167. Thus, a directional resistance Rx(i) is determined from position 169 to position X(i−1), Yj, Xk (one position less in the X direction), and a resistance Rx(i+1) is determined from position 169 to position X(i+1), Yj, Xk (one position greater in the X direction). Likewise, in the Y direction, a directional resistance Ry(j) is determined from position 169 to position Xi, Y(j−1), Zk, and a resistance Ry(j+1) is determined from position 169 to position X(i), Y(j+1), Xk. And in the Z direction, a directional resistance Rz(k) is determined from position 169 to position Xi, Yj, X(k−1), and a resistance Rz(I+1) is determined from position 169 to position X(i), Yj, X(k+1).

Once the resistance network determination algorithm 165 has determined these resistances, they can be stored in a resistance network database 170, as shown in FIG. 12. In the example shown, the resistance network database 170 associates each of the positions 167 (e.g., X1, Y1, Z1) with: a X-directional resistance (Rx1=A), which would comprise the resistance between X1, Y1, Z1 and its nearest neighbor in the X direction (i.e., X0, Y1, Z1); a Y-directional resistance (Ry1=B), which would comprise the resistance between X1, Y1, Z1 and its nearest neighbor in the Y direction (i.e., X1, Y0, Z1); and a Z-directional resistance (Rz1=C), which would comprise the resistance between X1, Y1, Z1 and its nearest neighbor in the Z direction (i.e., X1, Y1, Z0). Alternatively, each of these resistance values for each position 167 can be processed (averaged) to determine a resistance for a three-dimensional voxel in the tissue—e.g., a cubic voxel bounded by points X1, Y1, Z1 and X0, Y0, Z0.

The resistance network determination algorithm 165 can determine the resistance values in resistance network database 170 using a variety of mathematical techniques, as one skilled in the art will understand. For example, electrical resistivity tomography techniques can be used, as well as the related techniques of electrical impedance tomography and electrical capacitance volume tomography. See H. M. Loke, "Tutorial: 2-D and 3-D Electrical Imaging Surveys," (2004), published at https://sites.ualberta.ca/~unsworth/UA-classes/223/loke_course_notes.pdf; W. Daily et al., "Electrical Resistance Tomography—Theory and Practice," Near-Surface Geophysics Part 2: Applications and Case Histories, Chap. 17, pp. 573-98 (2005); "Electrical Impedance Tomography," published at https://en.wikipedia.org/wiki/Electrical_impedance_tomography; "Electrical Capacitance Volume Tomography," published at https://en.wikipedia.org/wiki/Electrical_capacitance_volume_tomography, all of which are incorporated by reference in their entireties. In accordance with these techniques, the resistance values in database 170 are computed by resistance network determination algorithm 165 by solving an inverse of a non-linear three-dimensional matrix that is not fully determined. As these techniques are well known, they are not described further.

The test procedure used to determine the resistances in resistance network database 170 can be initiated in different ways. In one preferred method, and referring to FIG. 6, the GUI 100 can include a selectable option 125 to start field modelling calibration. This will send a command from the clinician programmer 70 to the IPG 110 or ETS 150, and in particular to the field measurement algorithm 132 in those devices (FIG. 9), to begin measuring the voltage differential data 145, which data is then transmitted from the IPG 110 or ETS 150 to the clinician programmer 70 and processed (165) as just described to populate the resistance database 170. Preferably, field modeling calibration per option 125 precedes the actual determination of an electric field in the patient's tissue in response to a selected stimulation program for the patient, as described next. Although not shown, it should be understood that GUI 100 (FIG. 6) can include options to specify the particulars of the test procedure, such as defining an amplitude or other parameters for Itest; defining the electrode combination(s) Etest to which Itest will be applied; defining the voltage differential combinations Vex-Vey to be measured at each Itest; etc.

Once the test procedure is completed and the resistance network database 170 populated, the improved field modelling algorithm 160 can estimate an electric field in the tissue given a particular stimulation program chosen for the patient. Referring to FIG. 12, estimation of the electric field is determined using a field determination algorithm 175, which receives the direction resistances from database 170, and information regarding the patient's stimulation program. By way of review, the most relevant parameters from the stimulation program include the electrodes selected for stimulation (Es), and the (peak) amplitude (Is) (e.g., current) and polarity at each selected electrode, as entered for example into the stimulation parameter interface 104, although other stimulation parameters may also considered.

The field determination algorithm 175 simulates the provision of the current Is from the selected electrodes Es in light of the resistances as determined and stored in the resistance network database 170, and determines a voltage at three-dimensional positions 171 in the patient's tissue. In FIG. 12, positions 171 in the patient's tissue are shown as corresponding to the positions 167 (FIG. 13) used during the test procedure to determine the resistances in database 170. However, this is not strictly required, as the field determination algorithm 175 can readily compute equivalent directional resistances between positions 171 using the determined directional resistances between positions 167 in database 170.

The field determination algorithm 175 essentially solves, given the current Is provided from selected electrodes Es, voltage drops across the directional resistances, and so can compute a voltage at each position 171. Thus, at position X1, Y1, Z1, a voltage V=M is computed, at position X2, Y1, Z1, a voltage V=N is computed, etc. These voltages in three-dimensional space define a three dimensional-electric field 172 ($E(x,y,z)=dV/dx+dV/dy+dV/dz$). This electric field 172 can be provided to an image compilation module 180, which converts the electric field 172 data into an electric field image 112, complete with shading or colorization, and which can be rendered in the GUI (FIG. 6, 106, 108) as described earlier. As noted earlier, this preferably allows the user to see the electric field image 112 in the context of various tissue structures 114i. Further, the user can modify the stimulation program to modify the electric field and hence the electric field image 112 to understand the effect of such modification vis-à-vis such tissue structures 114i.

Figure 14C:
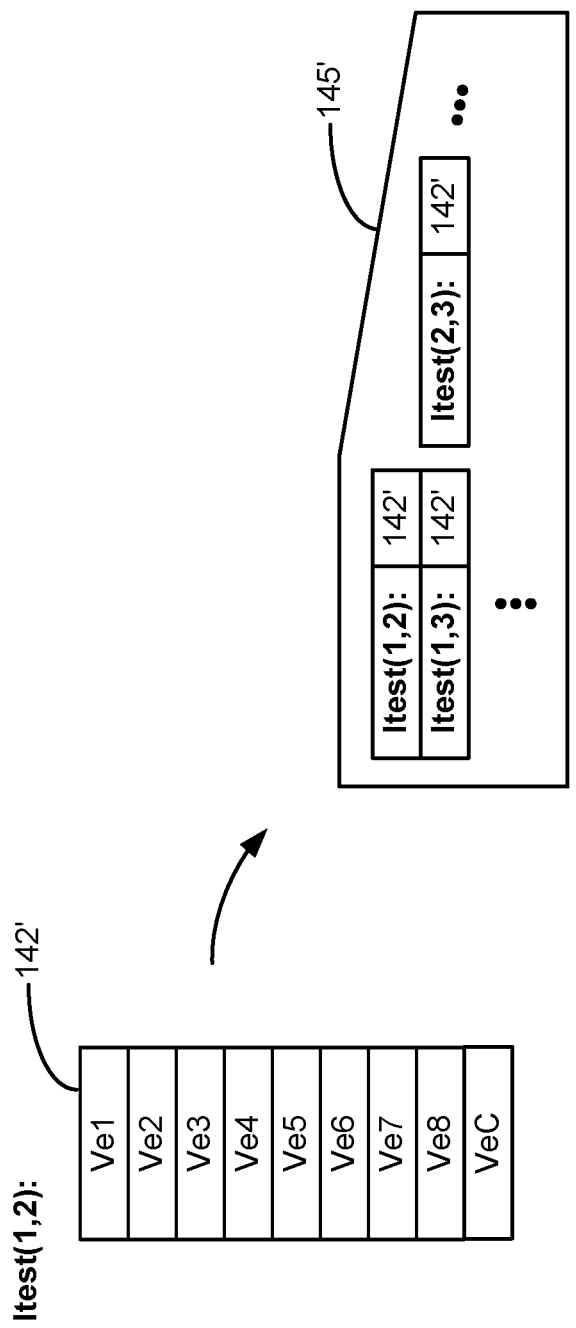

To this point in this disclosure, it has been assumed that the measurements taken by the field measurement algorithm 132 (FIG. 9) comprise voltage differentials, e.g., Vex-Vey. However, this need not be the case, and alternative examples are shown in FIGS. 14A-14C. In these examples, the voltages measured at the electrodes are single ended rather than differential. FIG. 14A modifies the multiplexer 138 to allow a ground reference potential (GND; 0 Volts) to be selected and passed to the amplifier 140. This allows the field measurement algorithm 132 to also select via control signals 137 one of the electrodes Ex (Vex), with the amplifier 140 then outputting the difference Vex, which can be digitized (ADC 136) as before). Alternatively, if only single ended measurements are to be made, the negative input to the differential amplifier can be hardwired to ground as shown in dotted lines, and in this case ground need not comprise an input to the multiplexer 138. Single ended voltage measurements can be taken with respect to reference potentials other than ground. For example, reference potential can comprise other voltages produced by the IPG 110 or ETS 150, or can comprise the voltage at another electrode, such as the case electrode Ec for example.

FIG. 14B is similar to FIG. 14A, but does not use a multiplexer 138. Instead, each electrode node ei has its own dedicated amplifier 140i, and control signals 137 can enable one or more amplifiers 140i to measure the voltage Vei at the electrodes, which voltages can again be digitized. In this example, the voltages at the electrodes can be measured at the same time (e.g., t1), rather than at subsequent Itest pulses (FIG. 10A).

FIG. 14C shows the resulting data set 142' taken at a particular test current Itest(1,2) applied between electrodes E1 and E2. In this example, the data set 142' merely comprises the voltages at the various electrodes (Ve1, Ve2, etc.) rather than a differential measurement between different electrode combinations. As before, these single ended voltage measurements can be taken for different electrode combinations of the test current (e.g., Itest(1,3), Itest(1,4), etc.), thus resulting in voltage data set 145'. As before, voltage data set 145' need not comprise all different electrode combinations, or single ended voltage measurements for all electrodes. Voltage data set 145' is preferably transmitted to the clinician programmer 70 for use by the resistance network determination algorithm 165 within the improved field modelling algorithm 160 (FIG. 12). If the resistance network determination algorithm 165 requires the use of voltage differentials, such differentials can simply be determined by algorithm 165. For example, from single ended measurements Ve1 and Ve2, the voltage differential of Ve1-Ve2 can be readily calculated, as can all other voltage differential combinations. Alternatively, the resistance network determination algorithm 165 may be configured to process single ended voltage measurements, and may not require voltage differential data per se.

Various aspects of the disclosed technique, including the field modelling algorithm 116 and the field measurement algorithm 132, and aspects used in the external devices to render and operate the GUI 100, can be formulated and stored as instructions in a computer-readable media associated with the clinician programmer system 70, the external controller 60, the IPG 110, or the ETS 150, such as in a magnetic, optical, or solid state memory. The computer-readable media with such stored instructions may also comprise a device readable by the clinician programmer system 70 or external controller 60, such as in a memory stick or a removable disk, and may reside elsewhere. For example, the computer-readable media may be associated with a server or any other computer device, thus allowing instructions to be downloaded to the clinician programmer system 70 or external controller 60 or to the IPG 110 or ETS 150 via the Internet for example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
    an implantable stimulator device, comprising:
        a plurality of electrode nodes, each electrode node configured to be coupled to one of a plurality of electrodes configured to contact a patient's tissue, and
        first control circuitry configured to execute an algorithm configured to provide a plurality of test currents, each test current provided between different combinations of at least two of the electrode nodes, and in response to the each of the plurality of test currents measure a plurality of voltages at different electrode nodes or at different combinations of the electrode nodes, the measured plurality of voltages comprising a voltage data set; and
    an external device configured to communicate with the implantable stimulator device, the external device comprising:
        second control circuitry configured to
            render a graphical user interface, wherein the graphical user interface comprises a first input to cause the first control circuitry in the implantable stimulator device to execute the algorithm,
            receive the voltage data set from the implantable stimulator device, and
            determine a representation of an electric field in the patient's tissue using the received voltage data set and using potential stimulation parameters for the patient.

2. The system of claim 1, wherein the external device is further configured to transmit the potential stimulation parameters to the implantable stimulator device for execution.

3. The system of claim 1, wherein the potential stimulation parameters comprise selected ones of the plurality of electrodes, and an amplitude of a current to be provided at each selected electrode.

4. The system of claim 1, wherein the graphical user interface further comprises at least one input to allow a user to enter the potential stimulation parameters.

5. The system of claim 1, wherein the second control circuitry is further configured to render the representation of the electric field as an electric field image, and to display in the graphical user interface the electric field image superimposed on a lead image showing the plurality of electrodes.

6. The system of claim 5, wherein the second control circuitry is further configured to render a tissue image, and to display the tissue image on the graphical user interface in relation to the electric field and the lead image.

7. The system of claim 6, wherein the graphical user interface further comprises one or more inputs to allow a user to adjust a view of the displayed tissue image, electric field image, and the lead image.

8. The system of claim 1, wherein the determined representation of the electric field is three-dimensional.

9. The system of claim 1, wherein the second control circuitry is further configured to define positions in three-dimensional space relative to the plurality of electrodes, and use the received voltage data set to determine a plurality of resistances between neighboring positions.

10. The system of claim 9, wherein the second control circuitry is further configured to determine the representation of the electric field by determining voltages at the positions in response to the potential stimulation parameters.

11. The system of claim 1, wherein the plurality of voltages are measured during each of the test currents.

12. The system of claim 1, wherein the plurality of voltages measured at different electrode nodes comprise single ended voltage measurements taken with respect to a reference potential.

13. The system of claim 1, wherein the plurality of voltages measured at different combination of the electrode nodes comprise differential voltage measurements.

14. The system of claim 1, wherein the plurality of test currents comprise current pulses.

15. The system of claim 14, wherein the current pulses comprise biphasic current pulses.

16. The system of claim 1, wherein the implantable stimulator device further comprises a conductive case for housing the first control circuitry, wherein the conductive case comprises one of the plurality of electrodes.

17. The system of claim 1, wherein the implantable stimulator device further comprises one or more implantable leads comprising the plurality of electrodes.

18. The system of claim 17, wherein the implantable stimulator device further comprises a fully-implantable pulse generator.

19. The system of claim 1, wherein the second control circuitry is further configured to
    receive from a database information indicative of three-dimensional positions of the plurality of electrodes, and
    determine the representation of the electric field in the patient's tissue using the received information, the received voltage data set, and the potential stimulation parameters for the patient.

* * * * *